United States Patent [19]

Reilly, Jr. et al.

[11] Patent Number: 4,542,234
[45] Date of Patent: Sep. 17, 1985

[54] PROCESS FOR THE SEPARATION OF (S,S) DIASTEREOISOMERS

[75] Inventors: Laurence W. Reilly, Jr., Yorktown Heights; Jeffrey N. Barton, New York, both of N.Y.

[73] Assignee: USV Pharmaceutical Corp., Tarrytown, N.Y.

[21] Appl. No.: 539,460

[22] Filed: Oct. 6, 1983

[51] Int. Cl.$^4$ ............................................ C07C 101/20
[52] U.S. Cl. ...................................... 560/38; 562/571; 562/443; 560/191
[58] Field of Search ............................................ 560/38

[56] References Cited

U.S. PATENT DOCUMENTS

| | | | |
|---|---|---|---|
| 3,887,606 | 6/1975 | Phillipps et al. | 560/38 |
| 3,976,680 | 8/1976 | Clark et al. | 560/38 |
| 3,983,162 | 9/1976 | Schlatter | 560/38 |
| 4,344,949 | 8/1982 | Hoefle et al. | 424/258 |

OTHER PUBLICATIONS

Patchett et al., "A New Class of Angiotensin-Converting Enzyme Inhibitors", Nature, vol. 288, (Nov. 20, 1980), pp. 280–283.

Noller, Chemistry of Organic Compounds, 3rd Edition, p. 359, (W. B. Saunders Co., 1965).

*Primary Examiner*—Bernard Helfin

[57] ABSTRACT

The (S,S) optical isomer of a compound having the general formula

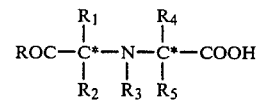

wherein R and $R_{1-5}$ are as defined herein, is recovered essentially free of the (R,S) and (S,R) isomers, by forming a solution of the esters of the (S,S) and the (R,S) and/or (S,R) isomers of said compound, selectively precipitating an acid salt (e.g. maleate) of the (S,S) ester from the solution, and treating the precipitate to form the desired free acid.

4 Claims, No Drawings

PROCESS FOR THE SEPARATION OF (S,S) DIASTEREOISOMERS

BACKGROUND OF THE INVENTION

The present invention relates to the manufacture of compounds which are useful intermediates in the synthesis of compounds having valuable pharmacologic properties, particularly as antihypertensive agents.

The intermediate of interest is the (S,S) diastereoisomer of compounds of the formula

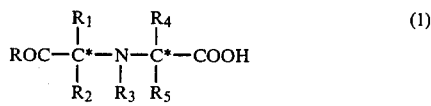

wherein R can be hydroxy, lower alkoxy, lower alkenoxy, di(lower alkyl)amino-lower alkoxy, hydroxy-lower alkoxy, acylamino-lower alkoxy, acyloxy-lower alkoxy, aryloxy, aryl-lower alkoxy, amino, lower alkylamino, di-lower alkylamino, hydroxyamino, or aryl-lower alkylamino;

$R_3$ can be hydrogen, lower alkyl, aryl-lower alkyl, cycloalkyl containing 3 to 20 carbon atoms, or fused aryl-cycloalkyl (hereby defined as a phenyl ring fused to a cycloalkyl ring containing 3 to 7 carbon atoms);

$R_1$, $R_2$, $R_4$, and $R_5$ can be independently any of the groups listed above for $R_3$, or alkenyl, or alkynyl;

wherein each alkenyl and alkynyl group contains 2 to 6 carbon atoms, each lower alkyl group and moiety contains 1 to 6 carbon atoms, and the groups can be substituted as described herein. The two asterisks denote the asymmetrical centers.

An intermediate of particular interest has the formula

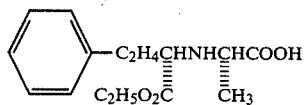

and is titled N-[(1S)-1-(ethoxycarbonyl)-3-phenylpropyl]-L-alanine. Hereafter, this configuration will be referred to as (S,S), in accordance with recognized terminology.

The free carboxylic group of compound (1) can be reacted with appropriately substituted amino compounds such as 1,2,3,4-tetrahydroisoquinoline-3-carboxylate, using standard peptide coupling techniques, to form compounds which are useful in treating hypertension. The resulting dipeptides, and their preparation from a compound having formula (2), are described in greater detail in Belgian Pat. Nos. 892,552 and 892,669 and U.S. Pat. No. 4,344,949. This U.S. patent also discloses that the particular stereochemistry shown in formula (2) above must be present in the dipeptide for biological activity.

One efficacious technique of obtaining the desired stereochemical configuration in the dipeptide is using an intermediate having formula (1) in the (S,S) stereochemical configuration. However, this technique is inefficient, in part because reactions to form compound (1) in its (S,S) configuration will form corresponding amounts of either the (R,S) or (S,R) diastereoisomer, depending on the configuration of the reactants, and separation of the (S,S) diastereoisomer has heretofore been low-yielding and tedious. Thus, it is desirable to be able to form the diastereoisomer of formula (1) by a process which is higher-yielding and less cumbersome than known processes.

SUMMARY OF THE INVENTION

The (S,S) diastereoisomer of a compound of formula (1) is recovered by treating a solution containing the (S,S) diastereoisomer of formula (1) or an ester thereof, which is in solution with the corresponding (R,S) and/or (S,R) diastereoisomer, so as to selectively precipitate an acid salt of the (S,S) diastereoisomer. The precipitation is highly stereoselective. Maleic acid is the preferred acid. The precipitated salt is then recovered, and where an ester has been precipitated it is converted to the (S,S) diastereoisomer of formula (1).

DETAILED DESCRIPTION OF THE INVENTION

As indicated, the present invention proceeds from a solution containing a mixture of (S,S) plus the (R,S) and/or (S,R) isomers, in which the substituents have the meanings given above for formula (1). The lower alkyl groups and moieties may be straight- or branched-chain, and include methyl, ethyl, propyl, isopropyl, butyl, isobutyl, t-butyl, amyl, hexyl, and the like. The alkenyl and alkynyl groups include vinyl, propenyl, allyl, isopropenyl, ethynyl, and the like. The alkyl, alkenyl, and alkynyl groups may carry substituents such as hydroxy, amino, lower alkoxy, mercapto, lower alkylthio, mercapto-lower alkyl, halogen, aryl, carboxy, carboalkoxy, carboxamido, and nitro.

The aryl-lower alkyl, fused aryl-cycloalkyl, and heterocyclic-lower alkyl groups include benzyl, phenethyl, naphthylmethyl, indolylethyl, indanylmethyl, indanylethyl and the like.

The cycloalkyl groups may be mono or polycyclic and contain from 3 to 20 carbons, preferably 3 to 7. These groups include cyclopropyl, cyclopentyl, cyclohexyl, cycloheptyl, bornyl, norbornyl, indanyl and the like. These groups may be partially unsaturated and carry substituents such as halogen, hydroxy, lower alkyl, lower alkoxy, thiol, lower alkylmercapto, nitro, hydroxyalkyl, and trifluoromethyl.

The aryl groups contain from 6 to 10 carbon atoms and include such groups as phenyl and α- or β-naphthyl and fused phenylcycloalkyl such as indanyl.

The aryl and aralkyl groups may carry one or more substituents such as lower alkyl, lower alkenyl, lower alkynyl, hydroxy, lower alkoxy, thiol, lower alkylmercapto, hydroxy-lower alkyl, thio-lower alkyl, nitro, halogen, trifluoromethyl, or methylenedioxy.

The acyl groups are preferably lower alkanoyl containing from 1 to 6 carbon atoms or benzoyl.

The halogen group may be fluorine, chlorine, bromine or iodine.

In the starting solution, the —COOH group can also be an esterified group —$COOR_6$. When R is hydroxyl, $R_6$ can be any of the substituents that $R_3$ can be. When R is not hydroxyl, $R_6$ should be selected so that when a compound with ester groups at R and $R_6$ is subjected to de-esterifying conditions (i.e. for conversion of an ester to a free acid (—COOH) group), the $R_6$ group converts preferentially rather than the R group. Examples of suitable groups for $R_6$ which meet this condition are benzyl, t-butyl, 2,2,2-trichloroethyl, and 2-trimethylsilylethyl; other suitable groups will be readily apparent to the skilled chemist. In the following description, the benzyl ester will be described for purposes of illustration, but equivalent ester groups are intended to be included within our invention.

The desired ester can be formed by reacting an α-halo ester of formula (3):

with an ester tosylate, e.g. the benzyl ester tosylate of formula (4):

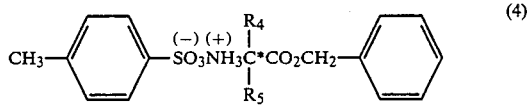

For instance, as is known in the prior art, compound (4) in which $R_4$ is hydrogen and $R_5$ is methyl can be formed by reaction of L-alanine, benzyl alcohol, and p-toluenesulfonic acid in a molar ratio of, e.g., 1:4:1 in a solvent such as toluene. Compound (3) can be prepared by known techniques; the halo group can be chloro, bromo, or iodo, and the preferred halo group is bromo. Those skilled in this art will recognize that it may be desirable to protect the more reactive substituents such as amino, aminoalkyl, and carboxy, by adding protective groups to ensure that the reaction proceeds at the desired sites, after which such groups are removed.

Those skilled in this art will also recognize that other synthetic routes can lead to the desired product; for instance, an amine of formula (5) can be reacted with an α-halo ester of formula (6).

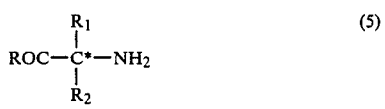

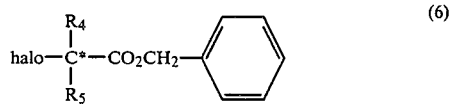

For purposes of illustration, the reaction of compounds (3) and (4) has been described, although the isolation of the (S,S) diastereoisomer by the process described herein can be applied to diastereoisomeric mixtures obtained via any synthetic methodology. If a diastereoisomeric mixture of the (R) and (S) forms of compound (4) or (5) is employed, then the reaction product will contain all four isomers (R,R), (R,S), (S,R) and (S,S). The (S,S) isomer can be recovered from the (R,S) and (S,R) isomers by the steps described herein. The (R,R) isomer can be expected to precipitate with the (S,S) isomer, although by selection of an appropriate optically active acid it would be possible to precipitate selectively the (S,S) from the (R,R) isomer as well. It is preferable, however, to avoid formation of the (R,R) isomer, and for this reason the asymmetric carbon adjacent to the nitrogen in compounds (4) and (5) above should be in the (S) (also termed (L)) configuration.

Compounds (3) and (4) are reacted in a suitable solvent such as dimethyl formamide, acetonitrile, lower alkanols, DMSO, ethyl acetate, or toluene. Sodium carbonate or another base should also be added, in order to consume acid formed during the reaction. The reaction mixture can be left at room temperature, but is preferably heated to a temperature such as 75°–100° C. which is high enough to increase the rate of reaction but not so high as to drive off the solvent. This reaction proceeds to completion in about 4 hours at approximately 86° C. The reaction mixture can then be diluted with, e.g., water and toluene, and partitioned between the aqueous and organic phases. The aqueous phase can be extracted a second time with, e.g., toluene to increase the yield. Other solvents that can be used besides toluene in the partitioning and washing include methylene chloride, diethyl ether, chloroform, and other water-immiscible organic solvents. The solvent should be non-polar, and the reaction mixture and the maleic acid or other acid used in the salt formation step should be soluble in it. Mixtures of solvents are also useful, provided the mixture meets the other criteria set forth herein.

The optical configurations of compounds (3) and (4) should be selected so that the product of the reaction between compounds (3) and (4) is a mixture which includes the (S,S) diastereoisomer of the compound of formula (1); both, or preferably one, of the (R,S) or (S,R) isomers will also be present, and usually one or more other by-products which are not of interest. While the (S,R) or (R,S) diastereoisomers are generally present in amounts approximately equimolar to the amount of the (S,S) isomer, the present invention is applicable to mixtures in which the ratio of the (S,S) to the other diastereoisomers present is 99:1 or higher to 1:99 or lower.

The desired (S,S) stereoisomer of the ester or acid of compound (1) is recovered by forming a salt of the mixed esters or acids with an acid in one, or a mixture, of the above-mentioned partitioning solvents, and selectively precipitating the salt of the (S,S) isomer from the solution. The invention is described below with reference to maleic acid salts, which are the most preferred, although it should be recognized that other acids which exhibit equivalent properties are to be considered within the scope of this invention. Among those so considered are tartaric, para-nitrocinnamic, cinnamic, hippuric, citric, and 2,4-dichlorobenzoic. This selective precipitation effectively recovers the (S,S) diastereoisomer from the mixture of compounds formed by reacting compounds (3) and (4); this advantage lets one use the raw reaction mixture and eliminates any need for preliminary isolation of a diastereoisomer or racemic mixtures thereof.

The maleic acid salt can be formed by adding maleic acid to the solution. Preferably, maleic acid is added as a solution in a solvent which meets the above-stated conditions, such as toluene or acetone. Alternatively, the solution can be prepared at a temperature at which maleic acid will dissolve, and the maleic acid can be added directly rather than as a preformed solution. Unless such moderately elevated temperatures are employed, room temperature is very satisfactory for the acid addition step. The amount of acid to add is not critical; however, the yield of the salt of the (S,S) diastereoisomer in the precipitation step increases as the amount of the acid that is added increases toward the total amount (in moles) of all diastereoisomers of formula 1. Amounts of acid up to about 10% higher than that total amount are tolerable, but beyond this point the excess of acid is wasted. To realize the most effective separation between the (S,S) diastereoisomer and the other diastereoisomers present, and to avoid co-precipitation of the (R,S) or (S,R) isomer, it is preferred that the total amount of dissolved solids not exceed about 25 wt. % of the solution. This can be assured by adding solvent as necessary. After the acid is added, the solution should be stirred to facilitate formation of the desired salt.

Addition of maleic acid as described herein readily forms the maleate salts of the (S,S) and the other diastereoisomers, evidently in relative amounts that are directly proportional to the relative amounts of the isomers present. The salt of the (S,S) diastereoisomer readily and selectively precipitates from the solution. Indeed, precipitation can be observed even before addition of the maleic acid is completed. The precipitation can be facilitated by cooling the solution below room temperature, e.g. to 0° to 10° C., and by seeding the solution in accordance with conventional practice for inducing precipitation. Virtually all of the maleate salt of the (S,S) isomer that forms precipitates from solution. In the precipitate the ratio of the (S,S) isomer to its (R,S) and (S,R) isomers is generally greater than 10:1, that is, the purity is at least 90 mol %, and preferably at least 95 mol %. The ratio of the (S,S) to the (R,S) and (S,R) isomers of the ester in the precipitate can be 50 to 100 times the ratio of the (S,S) to the (R,S) and (S,R) diastereoisomers in solution before the acid is added. Thus, the precipitate is enriched in the (S,S) isomer relative to the ratio of the (S,S) to the other isomers in the solution.

The precipitated salt is then recovered by filtration, and preferably washed with the solvent from which it was precipitated.

The precipitated salt thus recovered can be readily converted to the (S,S) isomer. For instance, the salt is partitioned between an alkaline aqueous solution and an organic phase, in order to convert the maleate salt to the free-base acid or ester compound. Suitable alkaline agents include ammonium hydroxide, sodium hydroxide, and sodium carbonate, preferably in amounts at least equal in moles to the amount of acid. Suitable solvents for forming the organic phase include water-immiscible, non-aliphatic liquids in which the compound is soluble, such as ethyl acetate, chloroform, toluene, methylene chloride, and diethyl ether. The organic phase is separated from the aqueous solution which is discarded.

Where the (S,S) compound that is recovered at this point has an ester group in the $R_6$ position, then following removal of the acid the compound is de-esterified to recover the free acid compound (1) in the (S,S) form. When $R_6$ is benzyl, de-esterification can be carried out by evaporating the organic partitioning solvent to recover the ester, and then dissolving the (S,S) ester in methanol or ethanol, adding palladium catalyst adsorbed on carbon, and carrying out catalytic hydrogenation in a known manner such as in a Parr pressure reactor vessel until the consumption of hydrogen ceases. The product is a solution of the (S,S) isomer of compound (1) in the methanol or ethanol solvent; the solution is filtered to remove the catalyst, and the solvent is evaporated to leave solid (S,S) compound (1). When $R_6$ is t-butyl, de-esterification can be carried out by acidification followed by recovery of the desired product, all by techniques well known in this art.

While the overall yield of the (S,S) isomer of formula (1) may not be 100% based on the starting materials (3) and (4), essentially all the yield loss is due to the reaction of compounds (3) and (4) rather than the steps of the present invention.

While the above description proceeds directly to the precipitation step without recovery of the diastereoisomeric mixture from solution, it should be recognized that the present invention also covers precipitation from solutions formed by dissolving diastereoisomeric mixtures of the acid of formula (1) or its $-COOR_6$ ester where the mixtures had previously been formed and recovered from solution.

The invention will be described in the following Example, which should be understood to be illustrative and not limiting.

EXAMPLE 1

A suspension of 405.5 g (1.50 mol) of ethyl 2-bromo-4-phenylbutyrate, 526.0 g (1.50 mol) of L-alanine benzyl ester p-toluenesulfonate, and 365.7 g (3.45 mol) of sodium carbonate in 2.25 liters of dimethylformamide was heated for 4 hours at 86° C. After cooling, the reaction mixture was diluted with 4.5 liters of water and 2.25 liters of toluene. After partitioning, the aqueous phase was extracted a second time with 0.5 liters of toluene The combined toluene phase was dried over anhydrous $MgSO_4$ and filtered, and the filter cake was washed with 125 ml of toluene. The solution produced thereby contained a mixture of the (S,S) and (R,S) isomers of the benzyl ester of compound (2). To this solution was added with stirring a previously prepared solution of 87.1 g (0.75 mol) of maleic acid in 450 ml of acetone. After seeding and stirring for several hours, the precipitate which had formed was collected, washed once with toluene and twice with hexanes, and dried to yield 166.0 g (0.341 mol) of the maleate salt of the (S,S) benzyl ester of compound (2) (m.p. 125°–126° C.). The overall yield was 23% based on the reactants, or 46% based on the expected yield of the (S,S) diastereoisomer.

$[\alpha]_D + 1.2°$, $[\alpha]_{365} + 21.3°$ (c 1.26, $CH_3OH$). Anal. calcd. for $C_{26}H_{31}NO_8$: C, 64.32; H, 6.44; N, 2.88. Found: C, 64.26; H, 6.33; N, 2.82.

166.0 g (0.341 mol) of the maleate salt thus produced was partitioned between 1.6 liters of methylene chloride and 1.6 liters of 10 wt. % aqueous ammonium hydroxide solution. The methylene chloride phase was dried over anhydrous sodium carbonate and filtered, and the filtrate was concentrated on a rotary evaporator to yield 136.5 g of a pale yellow oil. This oil was dissolved in 900 ml of absolute ethanol, and 9.0 g of 10% Pd-C was added. This reaction mixture was put on a Parr shaker for 1 hour, during which time hydrogen consumption ceased. Addition of ethanol and warming dissolved some product which had precipitated. The mixture was filtered through Celite, the solvent was evaporated on a rotary evaporator, and the resultant solid was collected and dried in vacuo at 55°–60° C. to yield 87.5 g (92%) of N-[(1S)-1-(ethoxycarbonyl)-3-phenylpropyl]-L-alanine (m.p. 141°–144° C.).

$[\alpha]_D + 26.6°$ (c 0.7, $CH_3OH$). Anal. calcd. for $C_{15}H_{21}NO_4$: C, 64.50; H, 7.58; N, 5.01. Found: C, 64.47; H, 7.47; N, 4.95.

What is claimed is:

1. A process for separating the (S,S) diastereoisomer of a compound of the formula

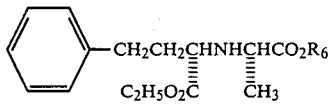

(A)

from a solution containing said (S,S) isomer and one or both of the corresponding (R,S) and (S,R) diastereoisomers in a non-polar, water-immiscible organic solvent selected from the group consisting of toluene, methylene chloride, diethyl ether, chloroform, ethyl acetate, and mixtures thereof, wherein $R_6$ is t-butyl or benzyl, comprising (i) reacting said diastereoisomers with an acid, selected from the group consisting of maleic, tartaric, p-nitrocinnamic, cinnamic, hippuric, citric, and 2,4-dichlorobenzoic acids, which forms acid addition salts with said diastereoisomers which salts are characterized in that the salts of the (R,S) and (S,R) diastereoisomers are soluble in said solution and said salt of the (S,S) diastereoisomer is not, under conditions wherein the salt of the (S,S) diastereoisomer selectively precipitates from said solution, and (ii) converting said precipitated salt to the (S,S) compound of formula (A).

2. The process of claim 1 wherein the acid is maleic acid.

3. A process for forming a compound of the formula

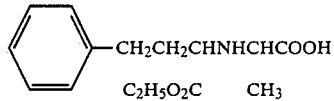

(B)

and having an (S,S) diastereomeric configuration, comprising (i) treating a solution of the (S,S) diastereoisomer of a compound of the formula

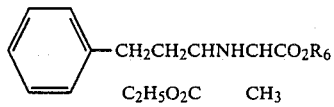

(A)

and one or both of the corresponding (R,S) and (S,R) diastereoisomers in accordance with the process of claim 1; and (ii) converting the (S,S) diastereoisomer obtained by said process into compound (B).

4. The process of claim 3 wherein the acid is maleic acid.

* * * * *